United States Patent
Frayssinhes et al.

(10) Patent No.: US 9,188,473 B2
(45) Date of Patent: Nov. 17, 2015

(54) APPARATUS AND METHOD FOR THE AUTOMATED DETECTION OF PHASES FOR AUTOMATED ANALYSIS

(75) Inventors: Daniel Frayssinhes, Roquemaure (FR); Yves Loire, La Queue en Brie (FR)

(73) Assignee: CYBIO FRANCE SARL, Savigny-le-Temple (FR)

( * ) Notice: Subject to any disclaimer, the term of this patent is extended or adjusted under 35 U.S.C. 154(b) by 314 days.

(21) Appl. No.: 13/811,336

(22) PCT Filed: Jul. 18, 2011

(86) PCT No.: PCT/FR2011/051709
§ 371 (c)(1),
(2), (4) Date: Jan. 21, 2013

(87) PCT Pub. No.: WO2012/010787
PCT Pub. Date: Jan. 26, 2012

(65) Prior Publication Data
US 2013/0292587 A1 Nov. 7, 2013

(30) Foreign Application Priority Data
Jul. 22, 2010 (FR) .................................. 10 56003

(51) Int. Cl.
*G01N 15/06* (2006.01)
*G01F 23/292* (2006.01)
*G01N 33/49* (2006.01)

(52) U.S. Cl.
CPC .......... *G01F 23/2928* (2013.01); *G01N 33/491* (2013.01)

(58) Field of Classification Search
CPC .................................................... G01F 23/2928
USPC ....................... 250/573–577; 356/239.6, 442; 73/61.41, 64.41
See application file for complete search history.

(56) References Cited

U.S. PATENT DOCUMENTS

| | | |
|---|---|---|
| 4,683,579 A | 7/1987 | Wardlaw |
| 5,279,150 A | 1/1994 | Katzer |
| 7,450,224 B2 | 11/2008 | Maroney et al. |
| 2003/0010941 A1* | 1/2003 | Spolaczyk et al. ............ 250/573 |
| 2004/0135090 A1* | 7/2004 | Itoh ........................... 250/357.1 |
| 2005/0163354 A1 | 7/2005 | Ziegler |
| 2007/0177778 A1 | 8/2007 | Massaro |
| 2009/0071225 A1* | 3/2009 | Schilffarth ..................... 73/1.02 |
| 2010/0007891 A1* | 1/2010 | Carroll et al. ................. 356/440 |

FOREIGN PATENT DOCUMENTS

| | | |
|---|---|---|
| WO | 94/14073 | 6/1994 |
| WO | 00/08472 | 2/2000 |

* cited by examiner

*Primary Examiner* — Thanh Luu
(74) *Attorney, Agent, or Firm* — Greer, Burns & Crain, Ltd.

(57) ABSTRACT

An apparatus and a method are provided for the detection of the level of the different phases present in at least one tube or vessel intended for filling the different wells of a microplate-format container for an automated analysis system. The apparatus is equipped with a fixing portion arranged to allow it to be itself held and/or handled instead of a microplate-format container, and carries out this detection by measuring the variation in wavelength of light reflected on a point zone of the content of the tube, during a displacement of the tube along an optical reader or of the optical reader along the tube in a rectilinear movement in a known manner.

Such a device or method is also operated by illumination with monochromatic light and detection of the amount of reflected light, with the phase differences being recognized by the sudden variation in the amount of reflected light.

16 Claims, 5 Drawing Sheets

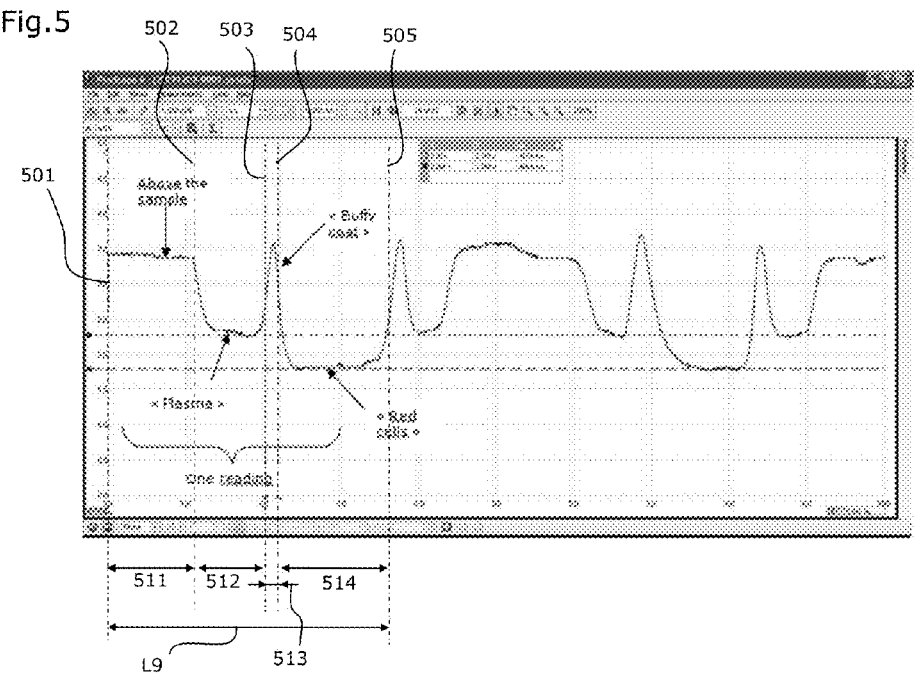
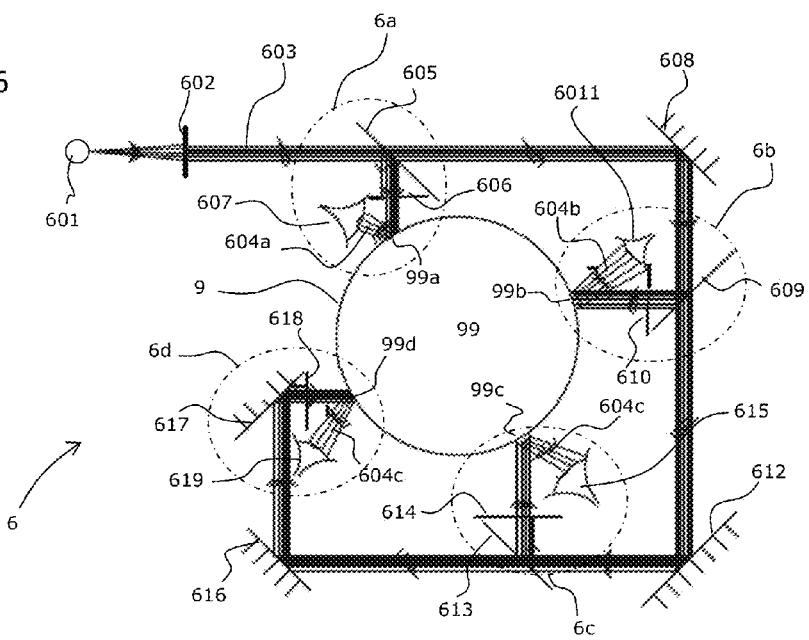

APPARATUS AND METHOD FOR THE AUTOMATED DETECTION OF PHASES FOR AUTOMATED ANALYSIS

BACKGROUND

The present invention relates to an apparatus and a method for the detection of the level of the different phases present in at least one tube or vessel the content of which is intended for filling the different wells of a microplate-format container for an automated analysis system. According to the invention, this detection is carried out by reflecting light on a point zone on the outside of the tube, during a displacement of the tube along an optical reader or the optical reader along the tube in a rectilinear movement and in a known manner.

It relates moreover to such an apparatus or method operating by illumination with monochromatic light and detection of the amount of reflected light, with the phase differences being recognized by the sudden variation in the amount of reflected light.

Increasingly, many methods in laboratory chemistry are automated, for example chemical analyses or DNA sequencing. The different products to be mixed together are handled by robotic equipment, and the entire procedure is controlled and monitored by computer. The rapid growth of large-scale DNA analyses, for example by PCR-type methods, has increased the requirements in this field and makes even the smallest improvement in the productivity and reliability of these procedures and the corresponding equipment worthwhile.

Within the technical capabilities of each facility, an effort is made, as far as possible, to carry out the procedure while minimizing the manual operations that give rise to loss of time and the risk of error.

Typically, an integrated automated facility is used that includes computerized monitoring of the products and samples processed. Such a facility comprises one or more robot operating heads, for example a pipetting instrument which takes an accurate shot of a liquid from a vessel in order to transfer it to another vessel, where a reaction will then take place. This vessel can then be moved to another slot for another operation, and/or stored in a waiting slot during the reaction, possibly in a reactor ensuring specific conditions of temperature, pressure, humidity, etc.

For reasons of reliability of analysis and productivity, receptacles of a standardized so-called "microplate" type are most usually used. Such a receptacle usually comprises a monolithic surface area pierced by a large number of wells of a few millimeters in diameter which are independent of each other. Other types of microplates also exist which are here included under the same name, for example a tray or rack comprising positions in which the same number of moveable individual tubes are inserted, and performing a function similar to the wells of a monolithic plate. Depending on the versions, a single plate can contain for example 96 or 384 wells. Several wells of a single microplate are often processed in parallel by multi-head pipetting instruments, which can be controlled together or separately.

These plates all have a single external geometry, in particular in their base footprint. This geometry is governed by a standard called "SBS" (ANSI/SBS 1-2004), which allows compatibility of all the plates with the majority of the robots and specialized machines in this field. This geometry comprises for example a rectangular base having two cut off chamfered angles, and is equipped with a rim having a slight horizontal extension around the base. This standardized shape allows all the compatible robots to use a robot arm equipped with a compatible slot for receiving, gripping and holding all the plates in a firm, precise and repeatable manner.

In some circumstances, and in particular for most analyses of blood or biological fluids, the automated analysis or processing comprises a separation phase, for example by centrifugation or decantation, which makes it possible to separate the different constituents present within the fluid initially taken.

For example in the case of blood, the initial sample is poured into a test tube, also called a sample tube, which is then centrifuged. The result of this centrifugation gives a distribution of the different constituents on several different levels, forming the following phases:

at the bottom of the tube is found a thick, dark red phase containing the red blood cells;

above this is found a thin, whitish phase forming a sort of emulsion called "buffy coat", which mainly contains white blood cells;

at the top is found a lighter red fluid phase formed by the plasma, which represents approximately 55% of the blood volume.

In order to use a single one of the constituents separated in this way, a pipetting instrument is used that is made to descend in the tube until reaching the depth where the constituent in question is found, for example into the buffy coat for sampling white blood cells. The component thus sampled is then poured into one or more receptacles, for example for a series of wells within a microplate, an operation which is often called "filling" the microplate.

In the centrifuged tube, the vertical position of the different phases varies according to many parameters, such as the initial amount of fluid or the diameter of the tube. In order to make it possible to automate sampling in a particular phase, it is therefore necessary for the robot to be provided with an apparatus for the detection of the levels of the different phases in each of the tubes to be sampled.

Different types of apparatus are known for carrying out this detection. Certain equipment measures for example the variation in the light transmitted by the content of the tube. These methods have drawbacks owing for example to the variability of the transmission factors. Furthermore, the transmission does not make it possible to distinguish between opaque phases even if they contain different constituents. Other methods measure fluorescence emitted by the content of the tube under chemiluminescence, but require relatively complex, costly high-power instruments for this purpose.

U.S. Pat. No. 4,683,579 proposes to measure the scattering of incident light of 400 to 1000 manometers at a narrow angle of the order of 20°. The precision of this technique however can be insufficient, and represents a significant space requirement around the tube which is inconvenient for incorporation in a robot system.

U.S. Pat. No. 7,450,224 proposes to carry out computerized graphical analysis of a complete colour image of the tube. For this purpose, the tube is gripped by a robot gripper and brought into an imaging chamber containing a CCD multipixel colour camera and uniform multidirectional lighting. The tube is extracted from a rack positioned on a table with XY displacement.

This technique however has drawbacks, for example requiring relatively costly components and complex computer processing requiring a certain computing power. Furthermore, such an apparatus permanently occupies a certain space and requires a table with robotized displacement in order to make an automated choice of the tube to be sampled.

SUMMARY

A purpose of the invention is to overcome all or part of the drawbacks of the prior art, in particular with respect to the following aspects:

simplicity, compactness, reliability;
versatility in use and for programming;
adaptation to the variability of the tubes, their positioning, the presence of opaque parts, such as a label;
adaptation to the presence or absence of requirements of the procedure carried out;
possibility of use in an integrated robot.

Furthermore, it is useful to be able to minimize the occupation of the operating heads available on a robot facility, for example in order to allow a better integration of the entire analysis procedure while reducing the limitation due to the number of available slots or operating heads.

The invention proposes an apparatus for the detection of the level of the different phases present in at least one tube or vessel, transparent or at least partially transparent and for at least certain wavelengths, the content of which is intended for automated filling of at least one analysis container for an automated analysis system, typically for filling the different wells of a microplate-format container. According to the invention, the apparatus comprises:

means for displacing the tube along an optical reader, or the optical reader along the tube in a known manner i.e. controlled or measured;
means for recording data representing the vertical position of at least one phase change within the content of this tube.

Preferably, the device is designed with kinematics carrying out a displacement of the tube in a rectilinear or substantially rectilinear movement, for example vertically.

In a variant, the movement can be designed to carry out a linear movement that is not rectilinear, and the recording means are arranged or programmed to adapt their calculation to the trajectory of the tube, for example by comparison with a chart or by a calculation formula taking account of the trajectory of the tube.

According to the invention, this apparatus operates by measuring the variation in wavelength of light reflected off the content of this tube. It is moreover equipped with a fixing portion arranged to allow it to be itself held and/or handled instead of a microplate-format container, for example by a robot arm provided for handling microplates.

Preferably, the apparatus is provided with displacement means operating along a single axis of displacement, or even a one-piece monaxial displacement actuator (outside of the gripping means).

The apparatus can thus be used for measuring the content of a conventional vessel arranged among others in a standard rack, within an automated procedure processing and managing all of these vessels.

It is thus possible to program the sampling of all the different phases, in each of the vessels of a rack, in order to fill one or more microplates and to carry out the analysis or the automated processing thereof, in a single automated global process.

The reading method allows a design that is relatively simple and compact as well as economic in comparison to other more elaborate techniques. It makes it possible moreover to detect differences between several opaque phases provided that they have different colours, unlike the technique using a transmission. This compactness facilitates the design of an apparatus the geometry of which is similar to the microplate format and suitable for the corresponding handlers.

This mechanical compatibility with the microplate format allows the use of the apparatus to be easily integrated into an overall cycle of automated processing. In fact, it is possible to fix it onto an existing operating head which can then be programmed to move and position it as required, according to the requirements of the procedure.

The apparatus itself can thus dispense with multi-axis and/or long-reach operating heads, as it can itself be displaced until close to the vessel to be measured. It is simpler, more compact and robust.

By placing the apparatus in a slot managed by the robot system, the problems of handling and picking up plates or containers in the automated cycle are limited or avoided, as well as the floor space occupied. Integration becomes more flexible and easier, in particular when a complete integrated facility is available that has a limited and compact workspace.

Furthermore, once in place on a microplate slot or "gripper" of the robot facility, the apparatus has its own means of gripping and moving the vessel to be measured. Thus the use of a second slot or robot operating head is avoided, or the shortage of one if there is no other available.

Furthermore, whenever the apparatus is not required, it is then possible to remove the apparatus in order to free up a microplate slot and save the space in a robot facility.

According to a feature, the apparatus comprises a base the lower periphery or footprint of which has a geometry compatible with the microplate format. These displacement means are moreover arranged to have access to the tube to be read via at least one displacement of the tube or of the optical reader situated in a region within and below said footprint.

Preferably, the displacement means have at least one so-called retracted position in which they do not extend below or outside the microplate-format footprint. These displacement means can for example be folded back into a base that does not extend beyond the outer and lower contours of the microplate-format footprint, and preferably within an upper protective casing.

The apparatus thus occupies only a small space during the movements of the arm which bears it and facilitates the organisation of the overall analysis or processing procedure.

It is apparent that in this way a compact, robust apparatus is obtained that is versatile in use and for programming, easy to handle and store without damage both by the robot and when it is not in operation.

In a preferred embodiment, the apparatus comprises means of gripping the tube, for example a pair of grippers, which have a geometry that is determined in order to allow them to be inserted from above around a tube arranged within a plurality of tubes that are substantially parallel inside a holding rack, for example vertical tubes in a horizontal rack.

In another embodiment (not shown), the displacement means move the optical reader along a tube situated below this apparatus. These displacement means and this optical reader together have a geometry that is determined in order to allow them to be displaced upwards, along a tube arranged within a plurality of tubes that are substantially parallel (for example in the same transverse plane, i.e. not longitudinal) within a holding container (for example vertical tubes in a horizontal rack).

This embodiment can also be combined with the previous one, for example in a configuration where the tube and the reader move in relation to each other and both move in relation to the base, and/or the frame.

According to the invention, the optical reader comprises at least one sensor detecting the wavelength of the light reflected by the content of the tube or at least by the outer surface of this content, in a determined restricted zone, mobile along said tube during the reading displacement.

According to a feature of the invention, the optical reader (14, 6) comprises a plurality of optical reading modules (6a to 6d) distributed in several different angular positions around the tube (9) and in the same horizontal plane, arranged in order to carry out a measurement in these different angular positions.

These modules can each comprise one or more sensors, and/or a light source.

The optical reader can also comprise one or more mirrors arranged around the tube so as to reflect the light originating from the source to a plurality of angular measurement positions distributed around the tube, and/or so as to send the light reflected by the content of the tube to a single sensor from a plurality of angular positions around the tube.

By combining several measurement points around the tube in this way, the invention makes it possible in particular to find at least one usable reading position even if the tube is not transparent over the whole of its periphery, for example as a result of a label stuck to its wall.

According to a preferred feature of the apparatus:
on the one hand, it comprises one or more light sources emitting only in a determined portion of the light spectrum; and
on the other hand, the optical reader comprises one or more reading modules each comprising one single-pixel sensor sensitive to the colour of said light source, for example a simple single photodiode.

The recording means are then arranged in order to use the amount of reflected light received by the sensor(s) to recognise the change in the wavelength of this reflected light.

At each moment the coloured light is reflected more or less according to the colour of the illuminated phase. The wavelength(s) of the coloured light are chosen as a function of the colour differences between the different phases the separation of which it is sought to detect.

Thus, if one phase is red and the other white, a blue light will be reflected much more by the white phase than by the red phase, which will thus appear much darker.

By detecting the marked variations in the amount of reflected light, with all wavelengths merged, it is then possible to note the colour change of the zone from which the measured reflected light originates.

It is understood that this type of detection allows a simple, compact and economic design, in particular from the point of view of the electronics, which contributes to the compactness of the assembly.

According to another aspect, the invention also proposes a method for detecting the level of the different phases present in at least one tube or vessel intended for filling the different wells of at least one container for an automated analysis system, said method comprising:
a displacement, in a rectilinear movement in a known manner, of the tube along an optical reader, or of the optical reader along the tube;
recording of data representing the vertical position of at least one phase change within the content of the tube.

According to the invention, this recording comprises a recording of the amount of light originating from a coloured source and reflected by the content of said tube at least one determined point that is mobile along said tube, i.e. mobile relative to the tube.

By reading point is meant a restricted zone, for example with respect to the dimensions of the tubes or the height of the phases measured in the tube. The measurement can also be done at several determined points, i.e. in that case in several restricted zones that are isolated from each other.

Various embodiments of the invention are envisaged, incorporating according to their possible combinations as a whole the different optional features disclosed herein.

BRIEF DESCRIPTION OF THE DRAWINGS

Other characteristics and advantages of the invention will become apparent from the detailed description of an embodiment which is in no way limitative, and the attached drawings in which:
FIG. 1 in the low position during the gripping of a tube,
FIG. 2 during reading while being raised,
FIG. 3 in the high position at the end of reading, and
FIG. 4 in the retracted position when a reading operation is not taking place;
FIG. 5 is a graph showing the results of the measurement of reflected light intensity, which are interpreted by the recording means in order to identify the position of the phase changes within the tube;
FIG. 6 is a diagrammatic top view showing an example of an optical reader having a single source and four reading modules each equipped with a single-pixel sensor, measuring at four different points;
FIG. 8, FIG. 9 and FIG. 10 are partial perspective views of an automated facility in different phases of filling operations according to FIG. 7, with:
in FIG. 8: detection of the phase levels in one of the tubes of a rack of tubes,
in FIG. 9: sampling of a phase in this tube according to the results of the detection,
and
FIG. 10: filling a microplate with the sampled phase.

DETAILED DESCRIPTION

Figure 1:
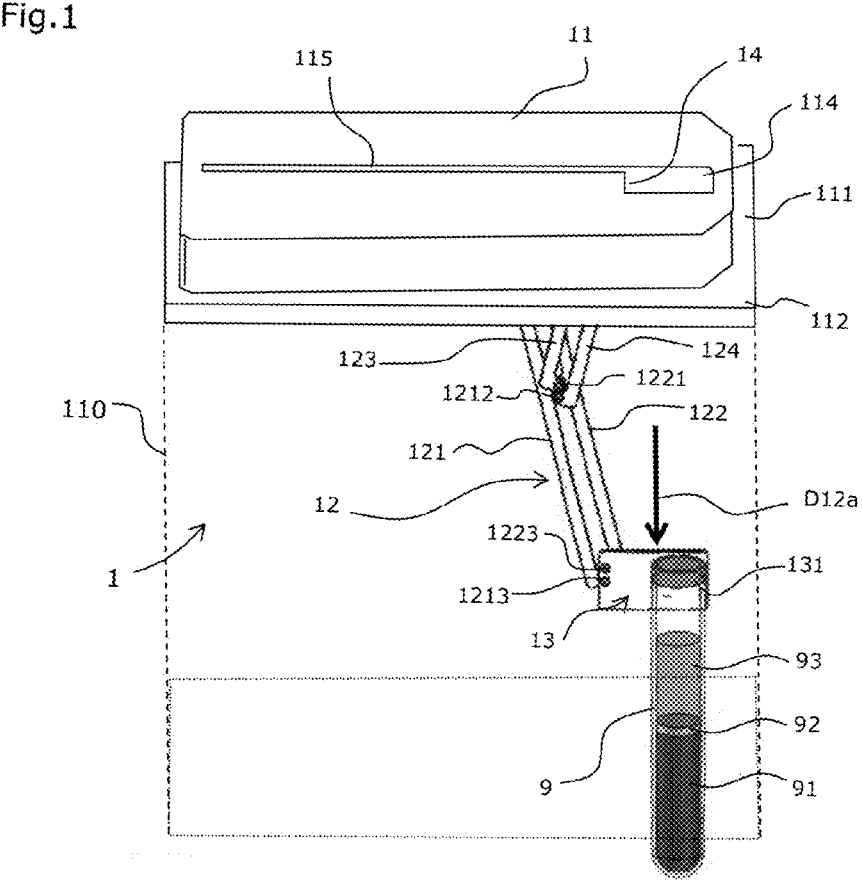
FIG. 1, FIG. 2, FIG. 3 and FIG. 4 are perspective views illustrating an example embodiment of the invention, in the following positions.
Figure 2:
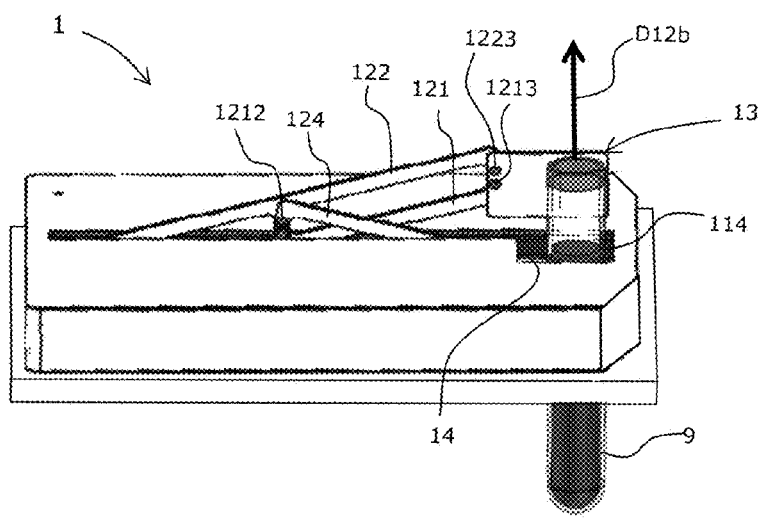
Figure 3:
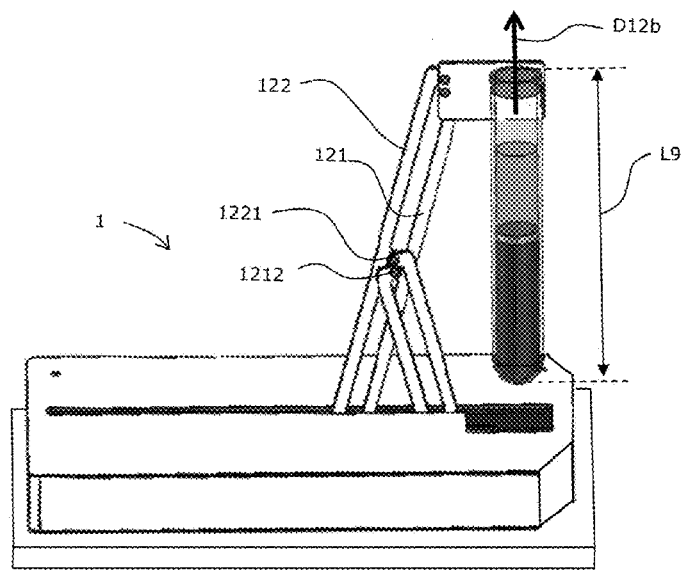

In the embodiment described here, the apparatus forms a "detection module" which can easily be mounted on a microplate slot for measuring with precision the heights of the different phases of a tube with a centrifuged blood sample. In order to carry out this measurement the "optical assembly" will travel the entire height of the tube. During this translational movement, the light reflection is measured and the position of the optical assembly relative to the tube at the moment of the changes in the level of reflection will determine the heights of the different phases.

The detection module has a device for gripping the blood sample tubes, making it possible to grip the tubes up to a distance for example of 100 mm below the module, in order to make them in their entirety transversally pass the detection module in order to carry out the phase detection. This gripping device is composed for example of a "lever" and a "gripper".

Once closed, the module has the complete format of a microplate (SBS format)

The phase detector can be used with a robotic arm within a robot platform. It can also be used alone, in which case the operator feeds the detector by hand, which will be mounted on a single base allowing the tube to rise and fall along the axis perpendicular to the light beam.

Detection by the phase detection module is based on a principle of absorption/reflection of a wavelength determined by the different phases of a tube containing a centrifuged blood sample. The different phases being, starting from the bottom of the tube: dark red (red blood cells), whitish (cell compounds including approximately 45% white blood cells), and reddish (plasma); the wavelength chosen here is in the blue region of the visible spectrum (400 to 500 nm). This wavelength is thus absorbed by the red blood cell and plasma phases and reflected by the cell compounds phase.

The tube is driven in a movement perpendicular to the axis of the light beam using a motorized arm, for example controlled by a microprocessor. This allows the exact position of each phase with respect to the top and/or the bottom of the tube to be known.

The measurement is made by detecting the amount of reflected light during the displacement.

FIG. 1, FIG. 2, FIG. 3 and FIG. 4 show a currently-preferred example embodiment of the invention.

In this embodiment, the apparatus comprises a base 11 the lower periphery or footprint of which has a geometry compatible with the microplate format. This geometry includes a rectangular form with standardized dimensions for this base, and comprises:
  on the one hand, a rectangular rim 111 extending around the base, and
  on the other hand, two adjacent angles of the base 11 each having a cut vertical face 112 of standardized dimensions, framing a short side of this base.

In this example embodiment, the displacement means 12, 13 comprise gripping means 13 of the tube 9, here a gripper formed by a plate 13 bearing an operating head equipped with a collar 131 that will grip the tube against the plate.

These gripping means are displaced by a mechanism 12 having mobile rods 121, 122, 123, 124 which are mobile within a rectilinear through-slot 115 arranged in the base 11.

These rods are linked together by pivot joints 1213, 1223, 1212, 1221 with axes perpendicular to the plane of displacement, producing a pantograph for displacement of the gripping means 13 or of the optical reader in a rectilinear direction D12a and D12b included in this plane of displacement P12 and parallel to the axis of the tube 9 to be read.

This mechanism 12 comprises in particular two main rods 121, 122 hinged in a parallelogram between the base and the gripping plate 13. This mechanism 12 comprises moreover two shorter secondary rods 123, 124, themselves hinged in a parallelogram between the base 11 and an intermediate or central portion 1221, 1212 of the main rods 121, 122.

On the extremity of the base, the ends of the two parallelograms are displaced in relation to each other by actuation means in order to vary the distance between them, thus upwardly displacing the gripping means 13. This variation is carried out for example by motor-driven endless screw, causing the end of the main parallelogram 121, 122 to slide along the slot 115 of the base, while the end of the secondary parallelogram pivots at a fixed point inside this slot.

In this figure, it is apparent that the displacement means 12, 13 allow access to the tube 9 to be read, by:
  a downward displacement D12a to reach and grip the tube, then
  an upward displacement D12b with the tube 9 which allows it to be extracted from its position longitudinally to its axis, then
  a further downward displacement (not shown) in order to return the tube to its place.

Figure 8:
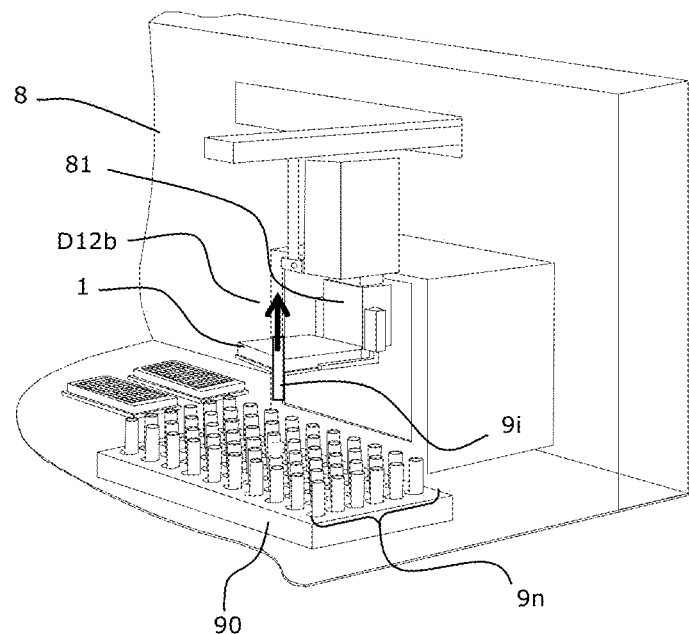

These different displacements are all situated in a region 110, shown in dotted lines, situated inside the footprint formed by the microplate-format geometry 111, 112 of the base 11. Gripping and extracting the tube take place more particularly below the base, which allows access to one or more tubes from above, even when they are closely arranged in a holding rack, as shown in FIG. 8.

Inside the microplate-format footprint (111), the slot 115 of the displacement mechanism 12 extends via a through-hole (114) sufficiently wide to allow the gripping means and the tube 9 to pass through during a complete vertical displacement.

Reading means 14 are arranged in the walls of this through-hole 114, so as to carry out the measurement during the passage D12b of the tube through this opening, in one direction or the other.

The reading means 14 are thus well protected, not very susceptible to damage and not very bulky.

Figure 4:
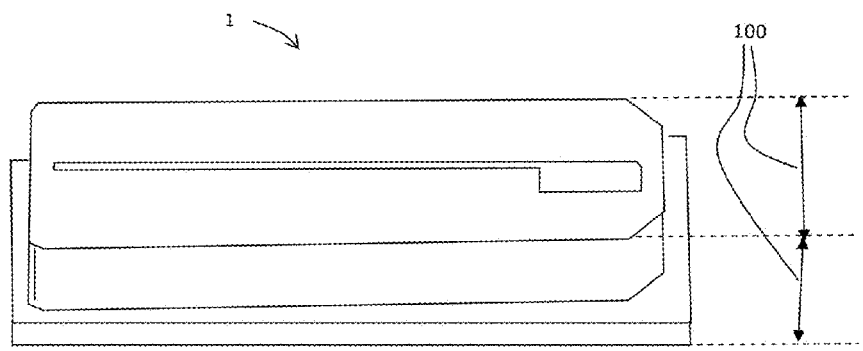

As is apparent in FIG. 4, the displacement means 12, 13 can be folded back into a so-called retracted position in which they do not extend below or outside the microplate-format footprint 111, or above a protective casing on the top of the base, the assembly having for example the standardized microplate dimensions 100.

When not in use, the apparatus forms approximately a simple and compact rectangular parallelepiped, without parts extending outside the rim 111, which is easy to handle and store without damage.

FIG. 6 shows an example of an optical reader having a single source and four reading modules each equipped with a single-pixel sensor, measuring at four different points.

In this example, the apparatus comprises on the one hand, a light source 601 emitting in only a determined portion of the light spectrum, and on the other hand, the optical reader 14, 6. This optical reader comprises here four reading modules 6a to 6d each comprising one single-pixel sensor 607, 611, 615, 619 sensitive to the colour of this light source, for example a photodiode.

The different sensors of the optical reader 14, 6 detect the wavelength of the light 604a to 604d reflected by the content 99 (essentially by its outer surface) of the tube 9 in a determined restricted zone 99a to 99d each forming a "reading point", each being mobile along the tube during the reading displacement D12b.

In this example, the light source 601 illuminates the furthest reading point 99d via a set of reflecting mirrors 608, 612, 616 and 618 forming an optical path for routing the illumination light 603 after collimation by a lens 602.

On this illumination light path 603, three semi-reflecting mirrors 605, 609 and 613 each become a part of the illumination light 603 in order to each illuminate one of the three other measurement points 99a, 99b and 99c.

Each of these reading points receives the illumination light through the restriction means which make it possible to limit the illuminated surface to the surface of the content 99 of the tube, for example collimation means or an aperture 606, 610, 614 and 618 respectively. It would also be possible to use a sufficiently narrow source such as a laser diode. The restricted zone has for example dimensions less than a circle of 0.5 or even 0.2 mm diameter.

In this way the different layers are illuminated using a light beam which will reflect the light in a different manner according to their constitution.

Each reading module 6a to 6d comprises one single-pixel sensor 607, 611, 615 and 619 respectively, which measures the light 604a to 604d reflected by its respective reading point 99a to 99d.

The recording means (not shown) are arranged and programmed to use the amount of reflected light 604a to 604d received by these sensors to recognise the change in the wavelength of the reflected light.

In the case of several sensors, a selection can be made between the different readers, or a mathematical or logic operation in order to provide a single result.

In this way "multiplexed photosensors" are produced, making it possible to measure the reflected light covering a periphery of a minimum 60% of this tube.

The different cell layers absorb a different amount of light according to their constitution and thus reflect an amount of light that is inversely proportional to the amount of light absorbed.

FIG. 5 shows the results of the measurement of reflected light intensity, which are interpreted by the recording means in order to identify the position of the phase changes within the tube;

As is apparent in the figure, the value of the amount of reflected light varies over the course of the displacement of the tube with respect to the reader.

Starting from the left of the figure, a first rising edge 501 corresponding to the detection of the top of the tube can be seen, followed by a plateau 511 corresponding to the empty part at the top of the tube.

A first falling edge 502 followed by a plateau 512 corresponds to the detection of the light red phase 93 of the plasma.

Two successive inverse edges 503 and 504 then form a region 513 that is sufficiently narrow to adopt the form of a peak, corresponding to the height of the whitish phase of emulsion or buffy coat 92.

The falling edge 504 and the plateau 514 then denote the dark red phase 91 of the red blood cells.

The following rising edge 505 denotes the passage of the lower end of the tube 9 in front of the optical reader 14.

This analysis of the edges and plateaus is programmed to provide a measurement of the heights and levels of the different phases present in the content of the tube 9, as well as the total height L9 of the tube.

By displacing the tube over its whole length, it is thus possible to know the total height of the tube and to disregard its variability from one tube to another. The device is then compatible with any tube height provided that the height is sufficient to be picked up by the "gripper" of the detector.

A computer generates digital data corresponding to the results of the measurement, for example a file indicating:
the height of the tube (difference between the highest point of the tube and the bottom of the tube);
the amount of reflected light in relation to a pre-defined height in mm.

This file is generated for example in a .txt, .csv, or .xml format, or any compatible format capable of being used in an automated pipetter.

It is thus possible to selectively pipette one phase or another, or even all three, in a manner that is precise and reproducible from tube to tube, and independently for each of the tubes according to the processing requirements.

Figure 7:
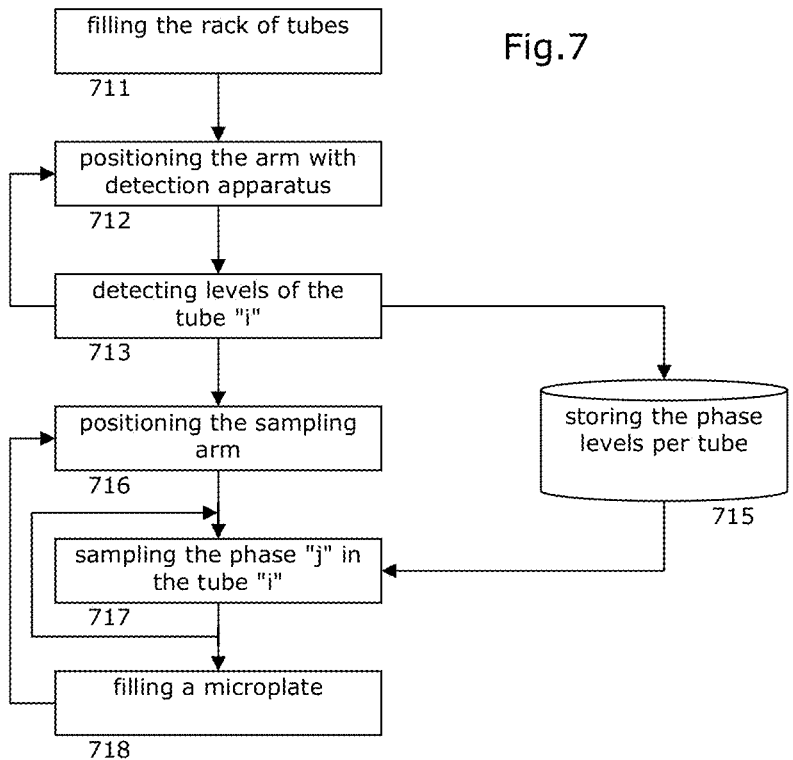
FIG. 7 is a flowchart showing filling operations in an analysis or processing method, comprising detection of phase levels in an embodiment of the invention.
Figure 9:
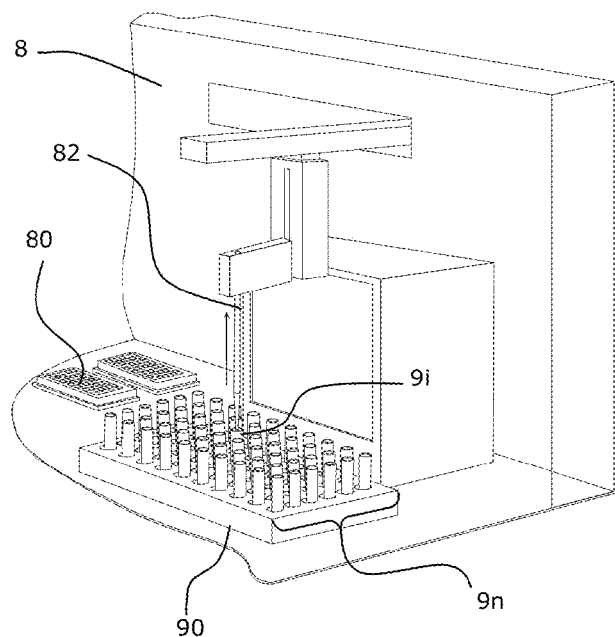
Figure 10:
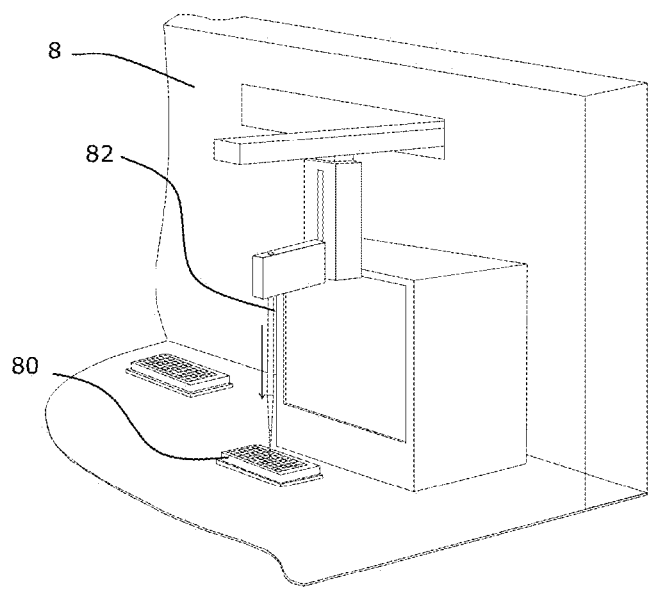

FIG. 7 shows the filling operations in an analysis or processing procedure in an automated facility, comprising detection of phase levels in an embodiment of the invention; FIG. 8, FIG. 9 and FIG. 10 show certain operations carried out during this procedure.

A filling step 711 comprises the filling of a rack 90 comprising a set of tubes 9n, in the working area of an automated facility 8. This rack 90 is placed in the entry of a detection apparatus 1 according to the invention, which is fixed to the gripper of a robot arm 81 of this facility 8.

The robot arm 81 positions 712 the detector 1 above a tube 9i chosen by the program.

The detector 1 extracts D12b the chosen tube 9i from the rack and carries out 713 the measurement of the levels of the different phases contained in this tube 9i, as well as the height of the tube.

These items of information are stored 715 associated with the references of the tube 9i.

These detection and storage steps can be repeated automatically for all of the tubes 9n contained in the rack 90.

Once all the tubes have been measured, an automated pipetting apparatus is positioned above the rack 90, or vice-versa.

For each chosen tube 9i, a pipetting point 82 is positioned 716 above the tube, and descends into in the tube to the depth necessary for accessing the chosen phase "j", on the basis of the information on the phase levels and height previously stored 715 for this same determined tube 9i. A chosen shot of the chosen phase is then sampled 717 by the pipetting tip.

This pipetting tip 82 will then fill an analysis container with the sampled shot of the chosen phase "j" from the chosen tube 9i, for example from one or more wells of a microplate 80.

These sampling and filling steps can be repeated automatically for all of the tubes 9n contained in the rack 90.

The filling procedure thus comprises a robotic sampling step 717 in the same tube 9i, detected, commanded or controlled based on the information 715 stored during the detection step 713.

It is understood that the invention allows an automated selection and sampling of one or more phases in one or more sample tubes, with a good adaptation of the automated methods to the variability of the tubes, their positioning, and to the presence of opaque portions, such as a label.

Of course, the invention is not limited to the examples which have just been described, and numerous adjustments can be made to these examples without exceeding the scope of the invention.

The invention claimed is:

1. An apparatus for detecting the level of the different phases present in at least one tube that is at least partially transparent and configured for automated filling of at least one analysis container in an automated analysis system, the apparatus comprising:
displacement means for displacing the at least one tube in a known movement of said optical reader along the at least one tube; and
data recording means showing the vertical position of at least one phase change within the content of the at least one tube,
wherein the apparatus measures, along said displacing, the variation in wavelength of a light reflected off the content of said tube so as to identify a vertical position of a color difference produced by the at least one phase change in the at least one tube, and wherein the apparatus
is equipped with a fixing portion arranged according to the microplate format so as to allow the automated analysis system to grip and handle the apparatus instead of a container with the microplate format.

2. The apparatus according to claim 1, wherein:
the fixing portion includes a base and the displacement means is secured to said base, said base having a lower periphery which has a geometry compatible with the microplate format;

wherein the displacement means are arranged to access the at least one tube to be read via at least one rectilinear displacement of the tube or of the optical reader, said displacement occurring within and below a lower periphery of said base.

3. The apparatus according to claim 2, wherein the displacement means have at least one retracted position in which the displacement means do not extend below or outside a lower periphery of said base.

4. The apparatus according to claim 1, wherein the displacement means comprise gripping means of the tube displaced by a mechanism having mobile rods in a single plane of displacement having a vertical component and pivot joints having axes perpendicular to said plane of displacement, producing a pantograph for displacement of the gripping means or of the optical reader in a rectilinear direction included in said plane of displacement and parallel to an axis of the tube to be read.

5. The apparatus according to claim 1, further comprising gripping means of the at least one tube having a determined geometry to allow the gripping means to be inserted from above around a tube arranged within a plurality of tubes that are substantially parallel inside a holding rack.

6. The apparatus according to claim 1, wherein the fixing portion includes at least one through-opening, wherein the displacement means are arranged for displacing the gripping means with the at least one tube through said at least one through-opening during, before or after at least partially during the course of a reading displacement.

7. The apparatus according to claim 1, wherein the displacement means displace the optical reader along the at least one tube situated below said apparatus, said displacement means and said optical reader together having a determined geometry to allow the displacement means to be displaced from above along a tube arranged inside a plurality of substantially parallel tubes within a holding container.

8. The apparatus according to claim 1, wherein the optical reader comprises at least one sensor detecting the wavelength of the light reflected by the content of the at least one tube in a determined restricted zone and mobile along said at least one tube during the reading displacement.

9. The apparatus according to claim 1, further comprising; one or more light sources emitting only in a determined portion of the light spectrum, wherein the optical reader comprises one or more reading modules each comprising one single-pixel sensor sensitive to the color of said light source, and the recording means are arranged to use the amount of reflected light received by the sensor(s) to recognize the change in the wavelength of said reflected light.

10. The apparatus according to claim 1, wherein the optical reader comprises a plurality of optical reading modules distributed in several different angular positions around the tube and in a single horizontal plane, arranged in order to carry out a measurement in these different angular positions.

11. The apparatus according to claim 1, wherein the optical reader comprises one or more mirrors arranged around the tube so as to reflect the light originating from the source to a plurality of angular measurement positions distributed around the tube, and/or so as to send the light reflected by the content of the tube to a single sensor from a plurality of angular positions around the tube.

12. A method for detecting the level of the different phases present in at least one tube or vessel intended for filling the different wells of at least one container in an automated analysis system, said method comprising:

displacing the at least one tube in a rectilinear movement and in a known manner along an optical reader, or displacing said optical reader along said at least one tube;

recording data representing the vertical position of at least one phase change within the content of said at least one tube;

said recording of vertical height comprising recording, along said displacing, the amount of light originating from a source, said light being colored and reflected by the content of said at least one tube at least one determined point, said point being mobile along and relatively to said at least one tube.

13. The method according to claim 12, further comprising a detection apparatus including a fixing portion arranged to allow the detection apparatus to be held instead of a microplate-format container, and displacement means for displacing said at least one tube in a rectilinear movement and in a known manner along an optical reader, or said optical reader along said at least one tube;

said method further comprising:
positioning a robot arm member comprising a slot at microplate format for receiving said detection apparatus, so as to be able to carry out a detection on a determined tube chosen within a plurality of substantially parallel tubes arranged within a holding rack;
detecting the levels of the chosen tube, comprising at least one of:
either an operation of upward extraction of said container and a displacement of the chosen tube in relation to the optical reader,
an operation of displacement of the optical reader by downward insertion along the chosen tube, and
a combination of these operations.

14. The method according to claim 12, further comprising analyzing the amount of reflected light, parametered to detect the position of at least one end of the tube, or to calculate the length of said tube.

15. An apparatus for detecting the level of the different phases present in at least one tube that is at least partially transparent and configured for automated filling of at least one analysis container for an automated analysis system, the apparatus comprising:

displacement means for displacing the at least one tube in a known movement along an optical reader; and data recording means showing the vertical position of at least one phase change within the content of the at least one tube, wherein the apparatus measures, along said displacing, the variation in wavelength of a light reflected off the content of said tube, and is equipped with a base arranged with a fixing portion according to the microplate format to be held by the automated analysis system instead of a container with the microplate format.

16. A method for detecting the level of the different phases present in at least one tube or vessel intended for filling the different wells of at least one container for an automated analysis system, said method comprising:

displacing the at least one tube in a rectilinear movement and in a known manner, along an optical reader; and recording data representing the vertical position of at least one phase change within the content of said at least one tube;

said recording of vertical height comprising recording, along said displacing, the amount of light originating from a source, said light being colored and reflected by the content of said at least one tube at least one determined point, said point being mobile along and relatively to said at least one tube; and detecting color variation by measuring an intensity variation.

\* \* \* \* \*